United States Patent
Van Gelderen et al.

(10) Patent No.: US 9,049,874 B2
(45) Date of Patent: Jun. 9, 2015

(54) USE OF AZAPERONE FOR REDUCING ANTIBIOTIC USAGE

(75) Inventors: Rainier Johannes Hendrikus Van Gelderen, Reusel (NL); Peter Meerts, Lokeren (BE)

(73) Assignee: Elanco Animal Health Ireland Limited, Sligo (IE)

( * ) Notice: Subject to any disclaimer, the term of this patent is extended or adjusted under 35 U.S.C. 154(b) by 597 days.

(21) Appl. No.: 13/119,736

(22) PCT Filed: Sep. 17, 2009

(86) PCT No.: PCT/EP2009/062045
§ 371 (c)(1),
(2), (4) Date: Mar. 18, 2011

(87) PCT Pub. No.: WO2010/031809
PCT Pub. Date: Mar. 25, 2010

(65) Prior Publication Data
US 2011/0172243 A1 Jul. 14, 2011

(30) Foreign Application Priority Data

Sep. 18, 2008 (EP) .................... 08164594

(51) Int. Cl.
| | | |
|---|---|---|
| *A61K 31/497* | (2006.01) | |
| *A23K 1/18* | (2006.01) | |
| *C07D 241/04* | (2006.01) | |
| *A23K 1/16* | (2006.01) | |

(52) U.S. Cl.
CPC ............... *A23K 1/1628* (2013.01); *A23K 1/184* (2013.01); *A23K 1/1893* (2013.01)

(58) Field of Classification Search
USPC .................................................. 514/253.01
See application file for complete search history.

(56) References Cited

FOREIGN PATENT DOCUMENTS

| JP | 2002/501019 A | 1/2002 |
|---|---|---|
| WO | 99/37297 A1 | 7/1999 |

OTHER PUBLICATIONS

Drugs in livestock feed (NTIS order, PB-298450, 1978, pp. 1-69).*
International Search Report relating to International Patent Application No. PCT/EP2009/062045. Date of Mailing of International Search Report: Oct. 27, 2009.
Written Opinion of the International Searching Authority relating to International Patent Application No. PCT/EP2009/062045. Date of Mailing of Written Opinion: Oct. 27, 2009.
Bjork, A.K.K., "Is Social Stress in Pigs a Detrimental Factor to Health and Growth That Can Be Avoided by Amerozide Treatment?", Applied Animal Behaviour Science, 1989, pp. 39-47, vol. 23(1-2), XP009107645.
Caccia et al., "Identification and quantitation of 1-arylpiperazines, metabolites resulting from side-chain cleavage of (4-substituted aryl-1-piperazinyl)aryl heterocyclic derivatives in rat plasma and brain." Journal of Chromatography, 1984, pp. 211-221, vol. 283, XP002501027.
"The Merck Index-Fourteenth Edition", 2006, p. 899, Merck Research Laboratories, XP002501028.
Gonyou et al., "Effects of amperozide and azaperone on aggression and productivity of growing-finishing pigs," J Anim Sci, 1988, 66(11):2856-2864.
Porter et al., "Azaperone: a review of a new neuroleptic agent for swine," Veterinary medicine, 1985, 80(3):88-92.

* cited by examiner

*Primary Examiner* — Layla Soroush
(74) *Attorney, Agent, or Firm* — James J. Sales; Elizabeth A. McGraw

(57) ABSTRACT

The present invention relates to a method for the reduction of antibiotic usage in animals through the use of orally administered azaperone.

6 Claims, No Drawings

USE OF AZAPERONE FOR REDUCING ANTIBIOTIC USAGE

CROSS REFERENCE TO RELATED APPLICATIONS

This application is the U.S. national stage of Application No. PCT/EP2009/0562045, filed Sep. 17, 2009, which application claims priority from EP 08164594.7, filed Sep. 18, 2008.

The present invention relates to a method for the reduction of antibiotic usage in animals through the use of orally administered azaperone.

Azaperone is a butyrophenone neuroleptic discovered in the early 1960s by Janssen Pharmaceutica laboratories and is currently available as the 4% sterile injectable solution called Stresnil™. Chemically, it is 4'-fluoro-4-(4-(2 pyridyl)-1-piperazinyl-butyrophenone and has the following structure:

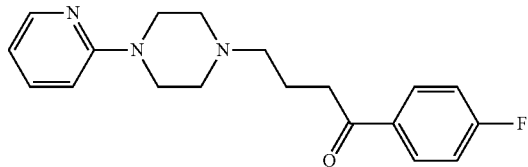 [SMILES: O=C(CCCN1CCN(c2ccccn2)CC1)c1ccc(F)cc1]

azaperone.

Stresnil™ (azaperone) injection is indicated for the prevention of aggressiveness and stress by inducing a variable degree of sedation. Following a single dose of Stresnil™, pigs may be mixed and fighting is eliminated or greatly reduced.

Stresnil™ injection is a potent sedative-tranquilizer which produces a predictable and consistent sedative response in pigs. The drug is fast acting, the onset of sedation is approximately 5 to 10 minutes after intramuscular injection. Within minutes after intramuscular administration, the animal becomes unsteady on its feet and lies down. The animal remains conscious but is quiet and indifferent to the environment. The degree of sedation is directly proportional to the amount of drug administered and the recommended dose of azaperone for the pig is 0.4 to 2 mg/kg of body weight.

Antibiotics are commonly administered to treat bacterial infections and are often administered to livestock by mixing it with food. However the use of antibiotics in the livestock industry is becoming problematic as it has been linked to the increased presence of antibiotic-resistant bacterial strains in humans, animals and in the environment. Additionally, antibiotic residues in meat are also of concern. Hence there is a need to find and develop methods for reducing the usage of antibiotics in the livestock industry.

The effects of the psychotropic drugs azaperone and amperozide in post-weaning pigs is described by Björk A. K. K. in *Applied Animal Behaviour Science*, 23, 39-47 (1989). Caccia S. et al. disclose in *Journal of Chromatography*, 283, 211-221 (1984) the identification and quantitation of metabolites of azaperone using biological samples from rats that were given orally azaperone.

It has now been found that the oral administration of azaperone in a low dose continuously provided together with food or drinking water results in a reduction of antibiotic usage in animals.

The term "antibiotic" refers to an antibacterial agent such as for example beta-lactam antibiotics such as benzylpenicillin, penethamate, fenoxymethylpenicillin, ampicillin, amoxicillin; cephalosporins such as cefalexin, cefquinome, cefovecin, ceftiofur; aminoside antibiotics such as paromomycin, gentamycin, apramycin, neomycin, spectinomycin; florfenicol; tetracyclines such as doxycycline, oxytetracycline, chlortetracycline; macrolide antibiotics such as acetylisovaleryltyrosin, erythromycin, spiramycin, tulathromycin, tylosin, tilmicosin; lincosamide antibiotics such as clindamycin and lincomycin; pleuromutilin antibiotics such as tiamulin and valnemulin; polymyxin antibiotics such as colistin; bacitracin; sulfamidin, thrimethoprim; (fluoro)quinolone antibiotics such as danofloxacin, difloxacin, enrofloxacin, flumequine, ibafloxacine, marbofloxacine, orbifloxacin or polypeptide antibiotics such as polymyxin B.

The term "animals" refers to any non-human warm-blooded animals in particular those produced for consumption such as poultry (chickens, turkey, ducks, ostrich, emu, quail etc.), and ruminants (goats, sheep, and cattle), pigs and rabbits.

In a first embodiment the present invention relates to a method of reducing the need for antibiotics to be given to an animal, the method comprises continuous oral administration of azaperone in a dose ranging from 0.5 mg per kg per day to 3.0 mg per kg per day.

Azaperone can be administered orally by mixing it with food or drinking water. Administration of azaperone through a water distribution system such as for providing drinking water is preferred. Many livestock farms are already equipped with the necessary devices to administer medication via drinking water hence no special modifications are needed to administer azaperone together with drinking water via the water distribution system. The dosing of azaperone can be adjusted in function of the water consumption of the livestock. For instance, piglets with a weight of 7 kg drink on average about 1.6 liter water per day. When azaperone is administered in a dose ranging from 0.5 mg per kg body weight per day to 3.0 mg per kg body weight per day this translates into a concentration of azaperone in the drinking water ranging from 2.2 to 13.1 mg per liter.

In a second embodiment the present invention relates to a method of reducing the need for antibiotics to be given to an animal, the method comprises continuous oral administration of azaperone in a concentration ranging from 2 mg to 13.0 mg per liter drinking water to said animal. In practice a concentration of about 6 mg azaperone per liter drinking water is typically used.

In a third embodiment the present invention relates to a method of reducing the need for antibiotics to be given to an animal, the method comprises continuous oral administration of azaperone at a dose ranging from 0.5 mg per kg per day to 3.0 mg per kg per day during a period from one to six days, more particular during a period of three days.

In a fourth embodiment the present invention relates to a method of reducing the need for antibiotics to be given to an animal, the method comprises continuous oral administration of azaperone at a concentration ranging from 2 mg to 13.0 mg per liter drinking water to said animal during a period from one to six days, more particular during a period of three days. In practice a concentration of about 6 mg azaperone per liter drinking water is typically used.

In another aspect the present invention relates to the use of azaperone as a medicament for use in the reduction of the need for antibiotics to be given to an animal wherein said medicament is continuously orally administered to said animal in a dose ranging from 0.5 mg/kg/day to 3.0 mg/kg/day. Azaperone can be adminstered orally mixed together with food or drinking water wherein the drinking water may be supplied through a drinking water supply system.

In a fifth embodiment the invention relates to the use of azaperone as a medicament for use in the reduction of the need for antibiotics to be given to an animal wherein said medicament is continuously orally administered to said animal in a concentration ranging from 2 mg to 13.0 mg per liter drinking water. In practice a concentration of about 6 mg azaperone per liter drinking water is typically used.

For administration with food, azaperone can be formulated in the form of a complete feed, a concentrate that is added to a feed product, a pre-mix that may be mixed with a feed product, or as a product which is applied or spread on top of a feed composition. Such formulations of azaperone suitable for administration with food can be made using art-known techniques.

For administration with drinking water or through a water supply system, azaperone is formulated in the form of a suitable concentrated water dilutable solution. An example of such a formulation is e.g.:

| Formula 1: (100 mg/ml): | |
|---|---|
| Azaperone | 100 mg |
| Citric acid | 80 mg |
| Methyl parahydroxybenzoate | 2 mg |
| Propyl parahydroxybenzoate | 0.2 mg |
| Purified water q.s. | 1 ml |

The effectiveness of orally administered azaperone through a drinking water system to to reduce the need for administration of antibiotics is demonstrated in the following example.

Preclinical Study of the Effects of Azaperone Administered Via Drinking Water

The study was performed in weaned pigs to investigate the effect of azaperone that was continuously orally administered via drinking water on postweaning diarrhoea and associated usage of antibiotics, behaviour, feed conversion, growth and homogeneity of growth.

Groups of approximately 250 pigs were enrolled in the study starting from the moment they were weaned. The pigs were housed according to everyday farming conditions in a conventional pig farm. All pigs were housed in similar buildings. Each group was housed in 2 compartments, gilts and barrows were housed in separate compartments. Pigs were kept in pens of approximately 12 individuals each.

After weaning, the piglets were housed in continuous artificial light for the first 48 hours. Afterwards, pigs were housed in continuous darkness for the further duration of the study, except during observations (twice a day). During the course of the study, pigs were not vaccinated. A metaphylactic colistine treatment via drinking water was applied in each group starting from the fifth day after weaning. Treatment continued for seven days.

Pigs were fed ad libitum. Troughs were filled automatically with a computerized system that records the supplied weight of feed per pen. During the first ten days of the nursery period, pigs were fed a pelleted weaner feed which had also been available to the piglets in the farrowing unit. Between the $10^{th}$ and $15^{th}$ day at the nursery, the weaner feed was gradually replaced by grower pellets which have been given until the $35^{th}$ day. Finally a switch was made between the $35^{th}$ and the $40^{th}$ day from grower pellets to starter pellets. Tap water was available during the whole period of the study and was supplied via a water nipple in the feeding trough.

The drinking water comprising azaperone was obtained by diluting Stresnil™ injection in water to obtain a concentration of 6 mg azaperone per liter drinking water. A primary dilution was prepared by diluting 90 ml of Stresnil™ 4% injectable solution with tap water to obtain 6 liters of preparation. This primary dilution was linked for 24 hours with an automatic dosing system which continuously diluted the preparation in the drinking water at a rate of 1 to 100. One preparation of the primary dilution was sufficient to treat 600 liters of drinking water which exceeded the anticipated daily consumed volume of water by the pigs in one compartment. The two following days, a new primary dilution was made fresh each morning and linked to the automatic dosing system for 24 hours.

This study was a controlled parallel study with 4 sequential groups of approximately 250 weaned pigs each. The first and third group were treated with azaperone via the drinking water for 3 consecutive days. The second and fourth group were control groups treated with placebo (plain drinking water).

TABLE 1

The following treatment groups can be distinguished:

| Group | Number of pigs | Number of pens | Treatment |
|---|---|---|---|
| 1 | 273 | 20 | placebo |
| 2 | 259 | 20 | azaperone |
| 3 | 255 | 20 | placebo |
| 4 | 240 | 20 | azaperone |

On day one of the test period, water containing 6 mg azaperone per liter or placebo, was made available. Starting from the fourth day, the drinking water no longer contained azaperone. All pigs followed the normal procedures for further fattening. No pigs were brought to the slaughterhouse during the study (3 days dosing and 39 days follow-up).

Diarrhoea Score Per Pen

In order to assess the effect of the oral azaperone administration on the onset of postweaning diarrhoea and concomitant therapeutic usage of antibiotics, the occurrence of diarrhoea was followed in groups 1 to 4 and recorded daily by the Principal Investigator. All individual pens were checked by the Principal Investigator and a diarrhoea score was noted as follows:

N=no diarrhoea

P=soft faeces

V=liquid faeces

Any use of antibiotics in groups 1 to 4 was recorded the first three weeks after weaning and grouping of the animals. The decision to treat an animal with antibiotics was made by the Principal Investigator according to everyday practice on that farm.

During the nursery period, a total of 26 placebo-treated piglets were treated with antibiotics for curative reasons and received a total of 29 individual injections (2×ampicilline, 22×enrofloxacine, 5×oxytetracycline). In the azaperone-treated group, 7 piglets received a total of 7 injections with antibiotics (1×ampicilline, 4×enrofloxacine, 2×ocytetracycline). The time points at which these therapeutic antibiotic injections were administered, are presented in Table 1:

TABLE 1

| | number of pigs treated | |
|---|---|---|
| week after weaning | placebo-treated group | azaperone-treated group |
| week 1 | 11 | 4 |
| week 2 | 14 | 3 |
| week 3 | 3 | 0 |

Therapeutic use of antibiotics during the first six weeks after weaning in placebo and azaperone-treated groups Conclusion: in this study it was observed that azaperone, when administered to weaned pigs via the drinking water at a dose of 6 mg/liter water during the first three days of a 42 day test period, resulted in an a significant reduction of the usage of antibiotics between the azaperone-treated groups compared to the placebo-treated groups both in the number of piglets treated (11 vs. 29) as well as in the number of individual antiobiotic treatments (13 vs. 33).

The invention claimed is:

1. A method of reducing the need to administer antibiotics to an animal, the method comprising continuous oral administration of azaperone together with food or drinking water to said animal in a dose ranging from 0.5 mg/kg/day to 3.0 mg/kg/day, wherein the animal is a pig.

2. The method of claim 1 wherein azaperone is administered through a drinking water supply system.

3. The method of claim 2, wherein said administration of azaperone to said animal is in a concentration ranging from 2 mg to 13.0 mg per liter drinking water, wherein the animal is a pig.

4. The method as claimed in claim 3 wherein azaperone is administered in a concentration of 6 mg per liter drinking water.

5. The method according to claim 1 wherein azaperone is administered during a period from one to six days.

6. The method of claim 5 wherein azaperone is administered during a period of three days.

* * * * *